(12) United States Patent
Overaker et al.

(10) Patent No.: US 7,022,129 B2
(45) Date of Patent: Apr. 4, 2006

(54) THREADED CABLE ANCHOR

(75) Inventors: David W. Overaker, Annandale, NJ (US); Yufu Li, Bridgewater, NJ (US); Ronald W. Marsh, Hackettstown, NJ (US); Kevin L. Cooper, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 33 days.

(21) Appl. No.: 10/112,618

(22) Filed: Mar. 29, 2002

(65) Prior Publication Data

US 2003/0187446 A1    Oct. 2, 2003

(51) Int. Cl.
*A61B 17/04*    (2006.01)
*A61B 17/56*    (2006.01)

(52) U.S. Cl. .......................... 606/232; 606/72
(58) Field of Classification Search ............... 606/73, 606/104, 232, 72, 60; 411/533, 516, 517
See application file for complete search history.

(56) References Cited

U.S. PATENT DOCUMENTS

| | | | |
|---|---|---|---|
| 4,870,957 A * | 10/1989 | Goble et al. .................. 606/73 |
| 5,156,616 A | 10/1992 | Meadows et al. | |
| 5,217,486 A | 6/1993 | Rice et al. | |
| 5,268,001 A | 12/1993 | Nicholson et al. | |
| 5,395,372 A | 3/1995 | Holt et al. | |
| 5,507,801 A * | 4/1996 | Gisin et al. .................. 606/86 |
| 5,662,658 A | 9/1997 | Wenstrom, Jr. | |
| 5,725,529 A | 3/1998 | Nicholson et al. | |
| 5,814,072 A | 9/1998 | Bonutti | |
| 5,868,789 A * | 2/1999 | Huebner ...................... 606/73 |
| 5,935,129 A | 8/1999 | McDevitt et al. | |
| 5,948,001 A * | 9/1999 | Larsen ........................ 606/232 |
| 5,948,002 A | 9/1999 | Bonutti | |
| 5,968,044 A | 10/1999 | Nicholson et al. | |
| 5,993,463 A * | 11/1999 | Truwit ........................ 606/130 |
| 6,033,430 A | 3/2000 | Bonutti | |
| 6,136,001 A | 10/2000 | Michelson | |
| 6,136,032 A | 10/2000 | Viladot Perice et al. | |
| 6,312,448 B1 | 11/2001 | Bonutti | |
| 6,554,852 B1 * | 4/2003 | Oberlander ................. 606/72 |
| 2002/0143329 A1 | 10/2002 | Serhan et al. | |

FOREIGN PATENT DOCUMENTS

WO    WO 97/29693    8/1997
WO    WO 01/06909 A3    2/2001

OTHER PUBLICATIONS

U.S. Appl. No. 10/609,336 "Surgical Anchor Inserter", filed Jun. 28, 2003.

* cited by examiner

*Primary Examiner*—Eduardo C. Robert
*Assistant Examiner*—Jessica R. Baxter

(57) ABSTRACT

A bone anchor for securing sutures or cables within a hole opening in a bone includes a screw element and a washer, which is separate from and independent of the screw element. The end of the cable to be secured within the bone hole opening is knotted or otherwise secured to the washer, thereby isolating the cable from the twisting of the screw element during insertion of the anchoring device into the hole opening in the bone.

13 Claims, 5 Drawing Sheets

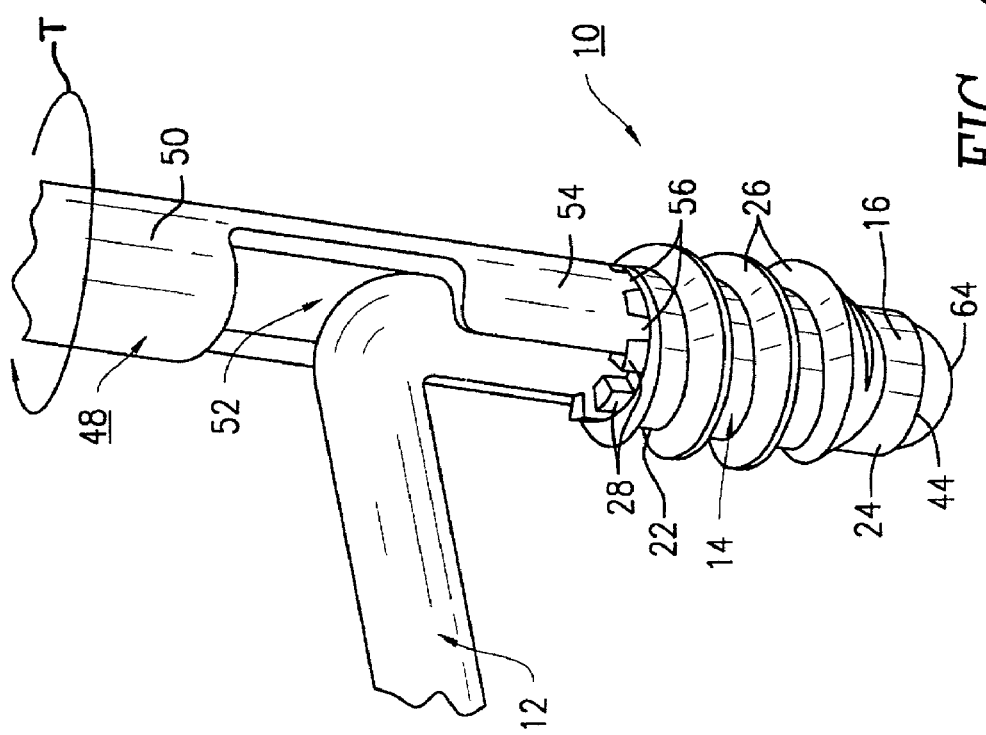
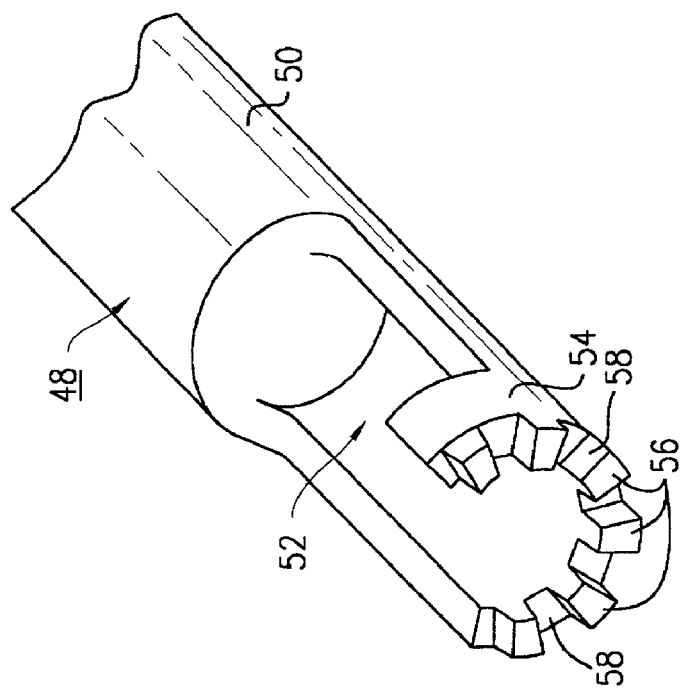

THREADED CABLE ANCHOR

FIELD OF THE INVENTION

The present invention relates to a bone anchor, and, more specifically, to a screw device for securing a cable within a hole opening in a bone.

BACKGROUND OF THE INVENTION

A wide variety of techniques are available to surgeons for securing sutures or cables within a hole opening in a bone. Screws, rivets, and other types of interference fitting anchors are commonly used.

The prior art is replete with bone fasteners that include screw elements having a threaded body. Typically, the cable, or suture, is directly attached to the screw element such as by threading the suture through an internal channel in the body of the screw. When the screw element is driven into the hole opening in the bone during insertion, the cable is twisted as the screw is twisted.

The prior art also describes bone screws in which the suture is not directly attached to the screw element. For example, U.S. Pat. No. 5,156,616 discloses a cannulated bone screw which retains a knotted suture and which is anchored to the bone. The bone screw is comprised of a body with an external thread and an internal axial passageway through the body. The passageway is larger in diameter at the distal end such that a suture passed through the body and then knotted cannot be removed therefrom. However, when the bone screw is twisted while being driven into the hole opening in the bone, the knot will twist, and the cable will also twist.

In the foregoing circumstances, what is needed is a fastener for securing a cable or suture within a hole opening in a bone such that the cable is isolated from the twisting of the fastener during insertion.

SUMMARY OF THE INVENTION

The problems and disadvantages of the prior art devices described above are overcome by the present invention through the provision of a bone anchor having a threaded body (e.g., in the form of a screw element) and a washer. A cable member is secured within a hole opening in the bone, such that an end tip of the cable member is knotted or secured to the washer to prevent separation therefrom. Because the screw element is rotatable independently of the washer, the cable member is isolated from the twisting of the screw element (i.e., it is not rotatable in response to the rotation of the screw element) during insertion of the anchor into the hole opening in the bone.

BRIEF DESCRIPTION OF THE DRAWINGS

Further objects, features and advantages of the present invention will become apparent upon consideration of the following detailed description of various exemplary embodiments considered in connection with the accompanying drawings, in which:

FIG. 3 is a perspective view of an insertion tool which constitutes another aspect of the present invention, the insertion tool being adapted for use with the bone anchor of FIGS. 1 and 2;

FIG. 4 is a perspective view of the bone anchor of FIGS. 1 and 2 assembled to a cable member and engaged by the insertion tool of FIG. 3;

DETAILED DESCRIPTION OF THE EXEMPLARY EMBODIMENT

Figure 1:
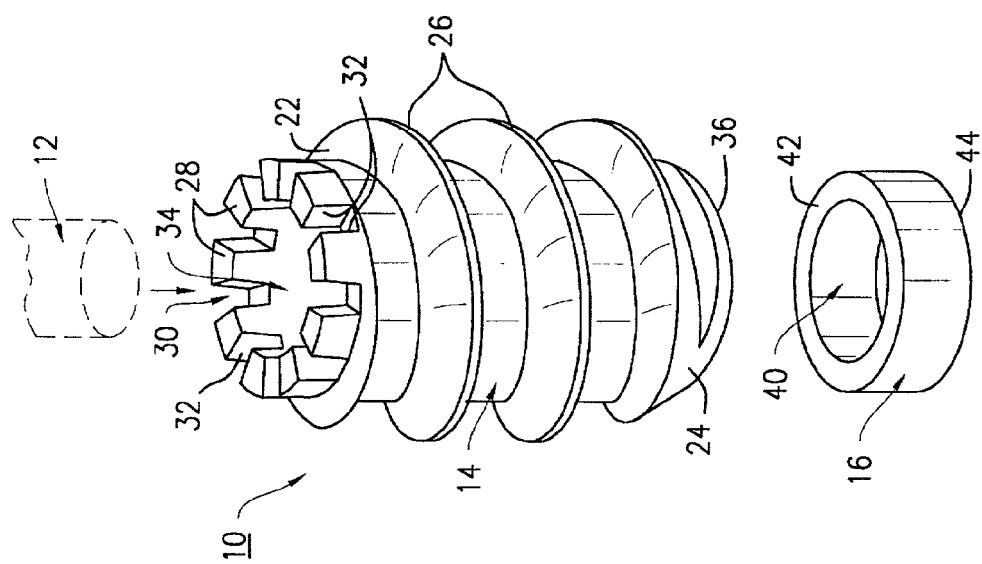
FIG. 1 is an exploded perspective view (looking from above) of a bone anchor which constitutes one aspect of the present invention, a cable or suture being shown in phantom to facilitate consideration and discussion.

Referring to FIG. 1, there is shown a bone anchor 10 for use in surgical procedures in the securing of a cable member 12 to a bone of an affected patient. The cable member 12 as used herein refers to a long, generally cylindrical fibrous structure such a braided or woven rope or suture.

The bone anchor 10 has two components: a threaded body 14 in the form of a screw element; and a washer 16. The cable member 12 passes through the screw element 14 and the washer 16, and is knotted beyond or attached to the washer 16. Because screw element 14 is rotatable independently of the washer 16, the cable member 12 is isolated from the twisting of the screw element 14 during the insertion of the bone anchor 10 into a hole opening of a bone (see FIG. 7).

Figure 2:
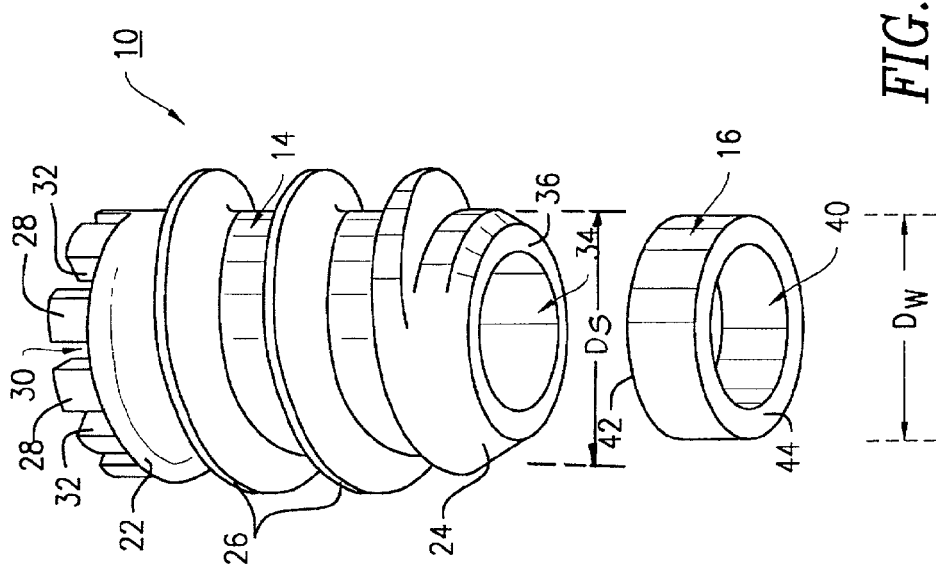
FIG. 2 is an exploded perspective view (looking from below) of the bone anchor of FIG. 1.

Referring to FIGS. 1 and 2, the screw element 14 is generally cylindrically shaped and includes a proximal end 22, a distal end 24, a helical thread 26 traversing the axial dimension of screw element 14, and a plurality of instrument engagement teeth 28. The teeth 28 include slots 30 bounded on opposite sides by walls 32, thereby imparting a castellated shape to the proximal end 22 of the screw element 14. The screw element 14 further includes an axial passageway 34 that passes entirely through the length of screw element 14. The helical thread 26 is preferably narrow in thread width and has a large thread pitch to allow the screw element 14 to cut into the soft bone of a patient. This allows the screw element 14 of the bone anchor 10 to be a self-tapping screw. The screw element 14 also includes a distal end surface 36 having a root diameter $D_s$ (see FIG. 2).

Figure 6:
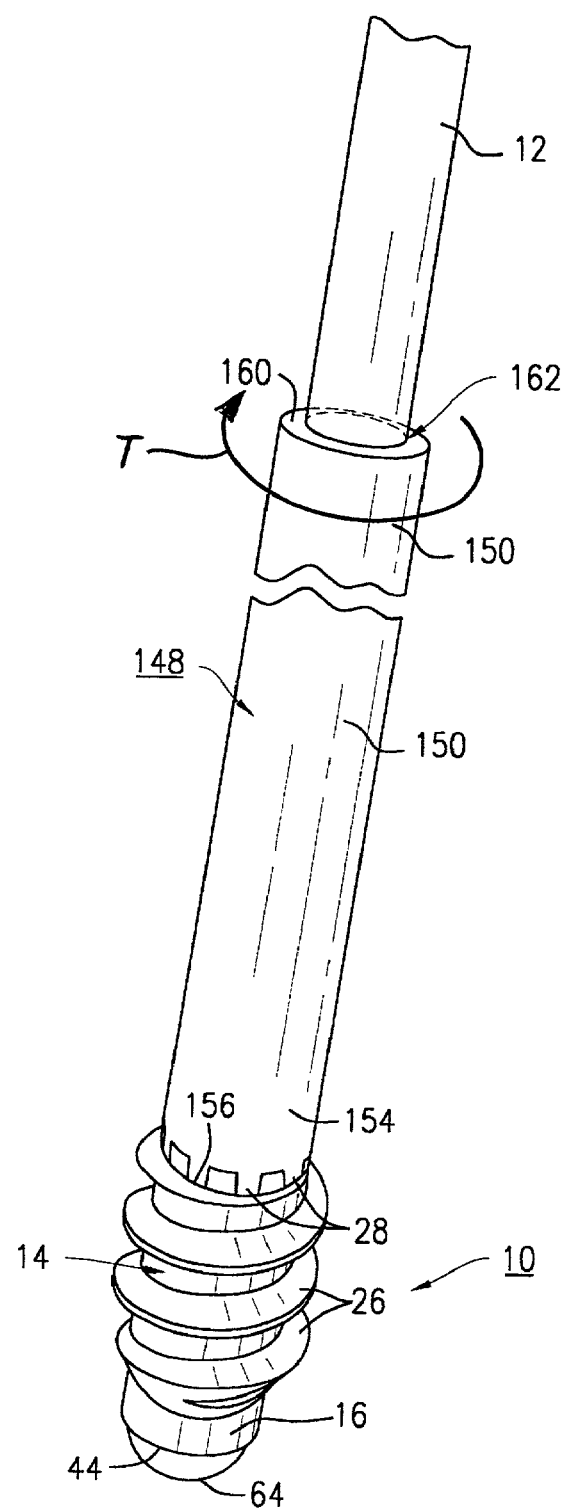
FIG. 6 is a perspective view of the bone anchor of FIGS. 1 and 2 assembled to a cable member and engaged by the alternate insertion tool of FIG. 6.

Referring still to FIGS. 1 and 2, the washer 16 has a generally cylindrical shape and includes an internal passageway 40, a substantially flat proximal surface 42, a substantially flat distal surface 44, and an outer diameter $D_w$. The proximal surface 42 of the washer 16 abuts and is in contact with the distal end surface 36 of screw element 14, when they are assembled as depicted in FIGS. 4 and 6. Additionally, the outer diameter $D_w$ of washer 16 is equal to or slightly smaller than the root diameter $D_s$ of screw element 14 such that the washer 16 will fit into a hole opening drilled in the bone of the affected patient, in which the screw element 14 is threaded into the bone via the helical thread 26.

Referring now to FIG. 3, there is shown an insertion tool 48 that can be used to drive the screw element 14 into the hole opening of the bone. The insertion tool 48 includes a rotatable shaft 50 having an opening 52 at its distal end 54. The insertion tool 48 also includes a plurality of prongs 56 protruding from the distal end 54 of shaft 50. The prongs 56 include spaces 58 therebetween, and as such the prongs 56 and the spaces 58 are configured such that they intermesh with the teeth 28 and slots 30 of screw element 14 for a purpose to be described hereinafter.

FIG. 4 shows the insertion tool 48 assembled to the screw element 14 with the prongs 56 and spaces 58 of insertion tool 48 fitting into and intermeshing with the slots 30 and teeth 28 of screw element 14, respectively. Thus, when a torque T is applied to the insertion tool 48 the resulting rotational motion is transmitted to the screw element 14 (i.e., the screw element 14 rotates conjointly with the insertion tool 48), whereby the screw element 14 cuts into the bone tissue. When using the insertion tool 48, the cable member 12 passes through the axial passageway 34 of screw element 14 and through the internal passageway 40 of washer 16, such that a cable tip 64 of cable member 12 resides just beyond the distal surface 44 of washer 16. The cable tip 64 may be a knot, a section of the cable member 12 that has been heated and slightly melted such that a diameter increase is gained (a process known as "tipping"), or a weld section to the distal surface 44 of washer 16. Cable tip 64 may also be formed by molding material onto the cable member 12. The function of cable tip 64 is to prevent the cable member 12 from being removed from the internal passageway 40 of washer 16. Also, other types of insertion tools can be used to engage the screw element 14 in order to turn the screw element 14 within the bone hole opening of the bone.

The shaft opening 52 of insertion tool 48 is provided so that the cable member 12 may turn away from the axis of the screw element 14 just above the proximal end 22 of screw element 14 (see FIG. 4). Insertion in such a case would require repeated engagement and disengagement of the insertion tool 48 with that of the screw element 14 in order to prevent the cable member 12 from winding-up or wrapping around on the insertion tool 48. Further details concerning the use and operation of the screw element 14 and the insertion tool 48 will be described hereinafter.

Figure 5:
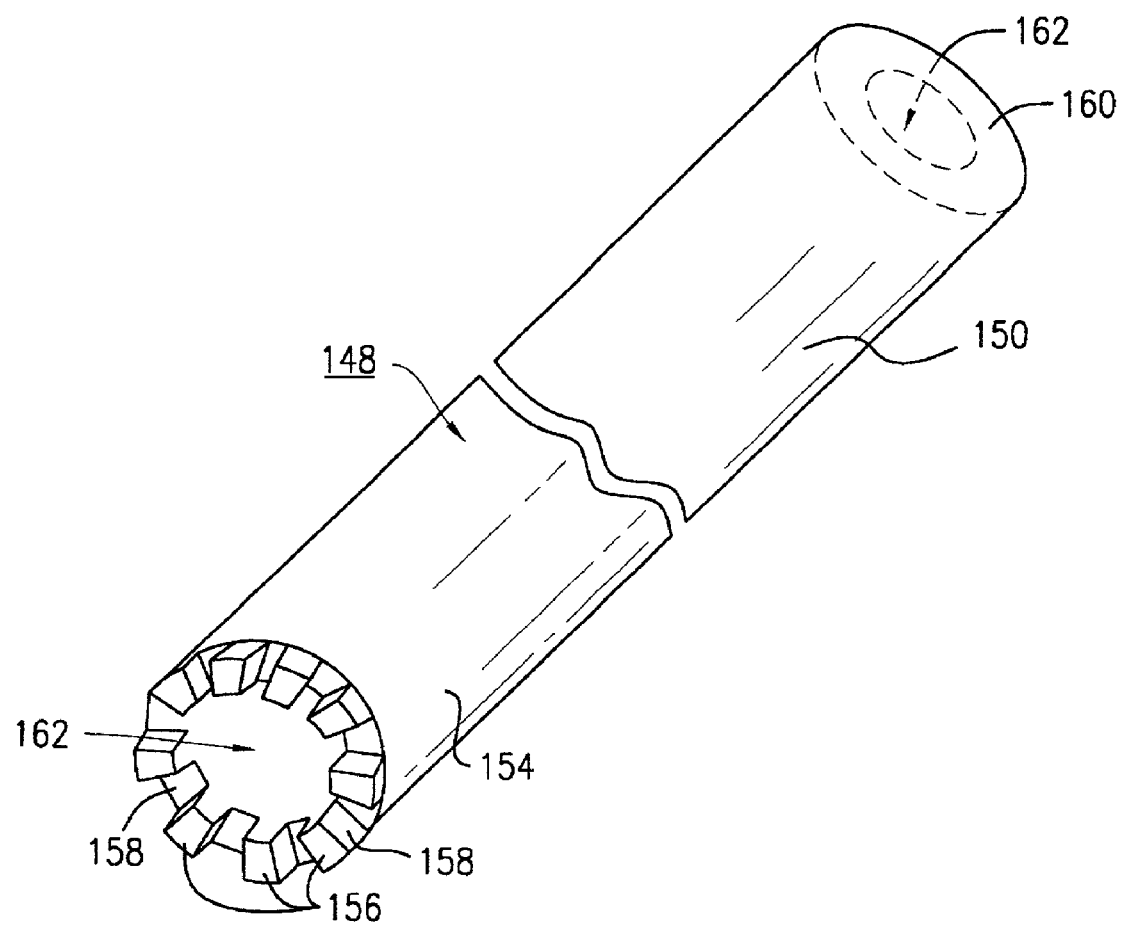
FIG. 5 is a perspective view of an alternate insertion tool.

With reference now to FIG. 5, an alternate insertion tool 148 of the present invention is shown. Elements illustrated in FIG. 5 which correspond to the elements described above with reference to FIG. 3 have been designated by corresponding reference numbers increased by one hundred. The alternate insertion tool 148 is constructed and operates in the same manner as the insertion tool 48, unless it is otherwise stated.

Figure 7:
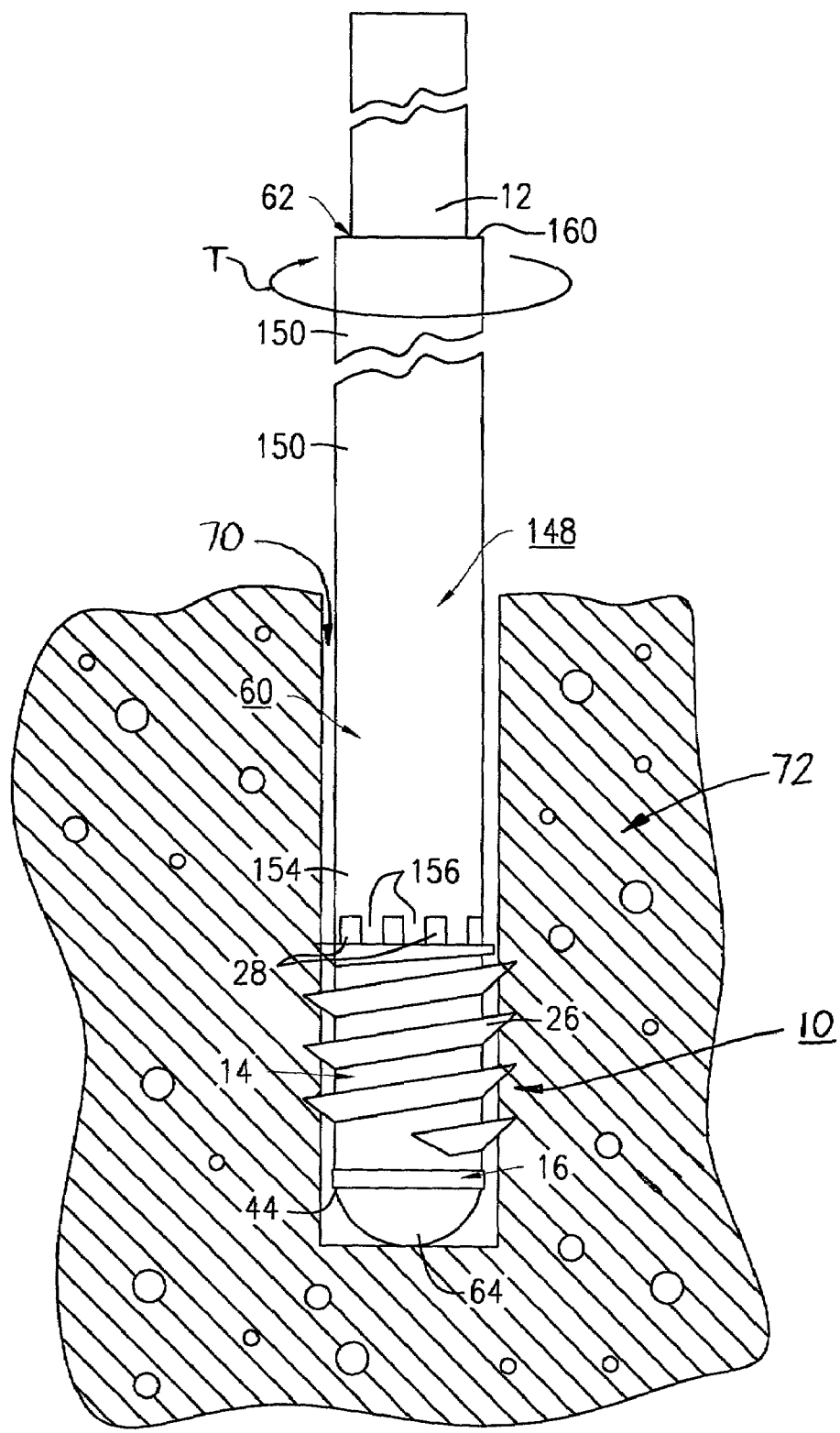
FIG. 7 is a side elevational view of the bone anchor assembly of FIG. 6 deployed for use within a bone hole opening.

As shown in FIG. 5, the alternate insertion tool 148 includes a proximal end surface 160 and an axial cannulation channel 162 (in place of the opening 52 at the distal end 54 of shaft 50) within shaft 150, and the remaining components of insertion tool 148 are exactly the same as insertion tool 48. The axial cannulation channel 162 traverses the axial length of shaft 150 such that cable member 12 would pass entirely through the alternate insertion tool 148. Insertion tool 148 would prevent the aforementioned problem of repeated engagement and disengagement of insertion tool 48 in preventing the cable member 12 from wrapping itself around the insertion tool 48. When using insertion tool 148, the cable member 12 passes through the axial passageway 34 of screw element 14 and through the internal passageway 40 of washer 16, such that the cable tip 64 of cable member 12 resides just beyond the distal surface 44 of washer 16. In operational use, as shown in FIG. 7, the bone anchor 10 would operate in the following manner. In a surgical procedure, the screw element 14 of the bone anchor 10 would be driven into a hole opening 70 drilled in the bone tissue 72 via the insertion tool 148 which includes a proximal end surface 62 and an axial canalation chamber 60. The insertion tool and the helical thread 26 of the screw element 14 would engage with the surrounding bone material and draw the screw element 14 further into the hole opening 70 of the bone 72. During the insertion of the screw element 14 into bone hole opening 70, the cable member 12 remains rotationally stable since it is attached to the washer 16. As the screw element 14 is further inserted into the hole opening 70 of the bone material 72, the cable member 12 is also drawn into the hole opening 70 of the bone 72. When the desired depth is reached, the insertion tool 148 is disengaged from the screw element 14 and is then removed from the hole opening 70 of the bone 72. The bone anchor 10 allows for the very precise depth placement of the cable tip 64 of bone anchor 10 and allows the easy backing out of the complete removal of the bone anchor 10 from the hole opening 70 of the bone 72, without damaging surrounding bone tissue 72.

Bone anchor 10 of the present invention may be used to secure suture or cable within a hole opening in bone for a variety of uses. Uses include reattachment of ligaments or tendons to bone. Furthermore, cable member 12 of bone anchor 10 could be connected to a second bone anchor (not shown), which is secured within a second hole opening in bone. This arrangement could be used, for example, to hold a bone block between adjacent vertebrae in spinal fusion procedures.

Suitable materials from which the bone anchor 10 may be formed include biocompatible polymers such as aliphatic polyesters, polyorthoesters, polyanhydrides, polycarbonates, polyurethanes, polyamides and polyalkylene oxides. The present invention also can be formed from absorbable glasses or ceramics comprising calcium phosphates and other biocompatible metal oxides (i.e., CaO), metals, combinations of metals, autograft, allograft, or xenograft bone tissues.

In the preferred embodiment, the bone anchor 10 is formed from aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, α,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

In another embodiment of the present invention, the polymers and blends can be used as a therapeutic agent release matrix. Prior to forming the bone anchor 10, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e., anticancer agents); anti-rejection agents; analgesics and analgesic combinations; anti-inflammatory agents; hormones such as steroids; growth factors, including bone morphogenic proteins (i.e., BMP's 1–7), bone morphogenic-like proteins (i.e., GFD-5, GFD-7 ana GFD-8), epidermal growth factor (EGF), fibroblast growth factor (i.e., FGF 1–9), platelet derived growth factor (PDGF), insulin like growth factor (IGF-I and IGF-II), transforming growth factors (i.e., TGF-β I–III), vascular endothelial growth factor (VEGF); and other naturally derived or genetically engineered proteins, polysaccharides, glycoproteins, or lipoproteins.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

It should be understood that the embodiments described herein are merely exemplary and that a person skilled in the art may make many variations and modifications without departing from the spirit and scope of the present invention. For instance, the castellated or toothed means for engaging the screw element with the insertion tool can be replaced by any other type of engagement means known to a person skilled in the art, such as a pin/hole combination. All such variations and modifications are intended to be included within the scope of the invention as defined in the appended claims.

We claim:

1. A bone anchor, comprising a screw element having a first passageway which extends axially through said screw element from one end thereof to an opposite end thereof; a washer having a second passageway which extends axially through said washer from one end thereof to an opposite end thereof, said one end of said washer being positionable adjacent to said opposite end of said screw element such that said first and second passageways are substantially aligned and such that said screw element is rotatable independently of said washer; and a cable member attached to said washer and passing through said first and second passageways such that said cable member is not rotatable in response to the rotation of said screw element.

2. A bone anchor according to claim 1 wherein said one end of said screw element has engaging means for engaging an insertion tool.

3. A bone anchor according to claim 2, wherein said engaging means includes a plurality of teeth arranged in a circular array on said one end of said screw element.

4. A bone anchor according to claim 3, wherein said one end of said screw element has a castellated shape.

5. A bone anchor according to claim 1 wherein said screw element is externally threaded.

6. A bone anchor according to claim 5, wherein said screw element is of a self-tapping type.

7. A bone anchor according to claim 5, wherein said opposite end of said screw element has a root diameter; and wherein said washer has a cylindrical outer surface with an outer diameter which is not greater than said root diameter of said opposite end of said screw element.

8. A bone anchor according to claim 1 wherein said screw element and said washer are made from a biocompatible material.

9. A bone anchor according to claim 8, wherein said biocompatible material is a biocompatible polymer.

10. A bone anchor according to claim 9, wherein said biocompatible polymer includes a therapeutic agent.

11. A bone anchor according to claim 1 wherein said cable member is attached to said washer at said opposite end thereof.

12. A bone anchor according to claim 11 wherein said cable member extends beyond said opposite end of said washer.

13. In combination, a bone anchor, comprising a screw element having a first passageway which extends axially through said screw element from one end thereof to an opposite end thereof and a washer having a second passageway which extends axially through said washer from one end thereof to an opposite end thereof, said one end of said washer being positionable adjacent to said opposite end of said screw element such that said first and second passageways are substantially aligned and such that said screw element is rotatable independently of said washer; a cable member attached to said washer and passing through said first and second passageways such that said cable member is not rotatable in response to the rotation of said screw element; and an insertion tool, comprising a rotatable shaft having a first opening at one end thereof, said first opening being sized and shaped so as to allow said cable member to pass therethrough, and engaging means, positioned on one end of said shaft, for engaging said bone anchor such that it can be rotated conjointly with said shaft in response to the rotation of said insertion tool.

* * * * *